United States Patent [19]
Dagan

[11] Patent Number: 6,146,629
[45] Date of Patent: Nov. 14, 2000

[54] HUMAN MONOCLONAL ANTIBODY AGAINST HEPATITIS B VIRUS SURFACE ANTIGEN (HBVSAG)

[75] Inventor: Shlomo Dagan, Rehovot, Israel

[73] Assignee: XTL Biopharmaceuticals Limited, Rehovot, Israel

[21] Appl. No.: 09/000,088

[22] PCT Filed: Jun. 10, 1997

[86] PCT No.: PCT/IL97/00183

§ 371 Date: Jan. 22, 1998

§ 102(e) Date: Jan. 22, 1998

[87] PCT Pub. No.: WO97/47653

PCT Pub. Date: Dec. 18, 1997

[30] Foreign Application Priority Data

Jun. 11, 1996 [IL] Israel ......................................... 118626

[51] Int. Cl.$^7$ ........................ A61K 39/42; A61K 39/395; C12N 5/06; C12N 5/16
[52] U.S. Cl. ..................... 424/149.1; 424/130.1; 424/141.1; 424/133.1; 424/142.1; 424/161.1; 435/70.21; 435/326; 435/339
[58] Field of Search ............................. 424/149.1, 142.1, 424/161.1, 133.1, 130.1, 141.1; 435/70.21, 326, 339

[56] References Cited

U.S. PATENT DOCUMENTS

| | | | |
|---|---|---|---|
| 4,714,613 | 12/1987 | Shouval | 424/86 |
| 4,778,761 | 10/1988 | Miyanohara | 435/320 |
| 4,883,752 | 11/1989 | Eda | 435/68 |
| 5,223,263 | 6/1993 | Hostetler | 424/450 |
| 5,565,354 | 10/1996 | Ostberg | 435/240.27 |
| 5,648,077 | 7/1997 | Ostberg | 424/149.1 |

FOREIGN PATENT DOCUMENTS

| | | | |
|---|---|---|---|
| 179 483 | 4/1985 | European Pat. Off. | |
| 0179483A | 4/1986 | Japan | C12P 21/00 |
| 9411495 | 5/1994 | WIPO | C12N 5/20 |
| 94/26784 | 11/1994 | WIPO | |

OTHER PUBLICATIONS

Ehrlich et al. 1992 Human Antibodies and Hybridomas vol. 3 p 2–7, Jan. 1992.

Ehrlich et al. Hum. Antibod. Hybridomas 3: 2–7, 1992.

*Primary Examiner*—Michael P. Woodward
*Assistant Examiner*—Mary K Zeman
*Attorney, Agent, or Firm*—Browdy and Neimark

[57] ABSTRACT

Disclosed is a hybridoma cell line which produces human antibodies capable of binding to the hepatitis B virus surface antigen (HBVsAg), as well as antibodies produced by the cell line. Also disclosed are various uses of said antibodies in the prevention and treatment of HBV infection. Peripheral blood lymphocytes obtained from human donors having a high titer of anti HBVsAg antibodies are activated in vitro with pokeweed mitogen and then fused with heteromyeloma cells to generate hybridomas secreting human antibodies having a high affinity and specificity to HBVsAg.

11 Claims, 7 Drawing Sheets

FIG.1A
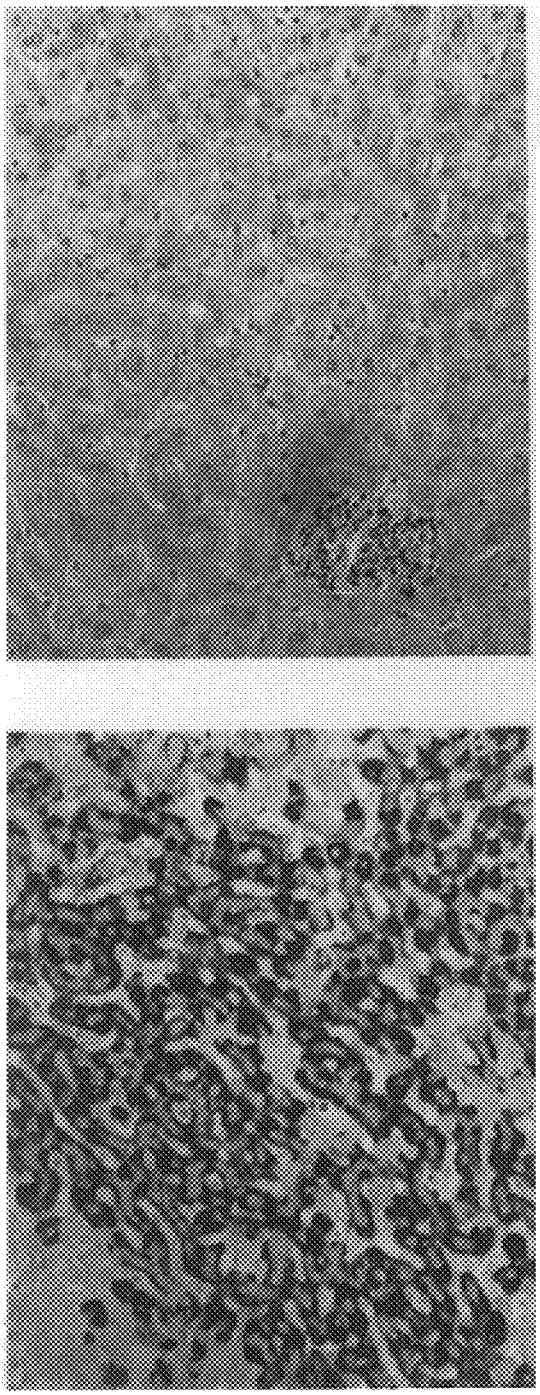
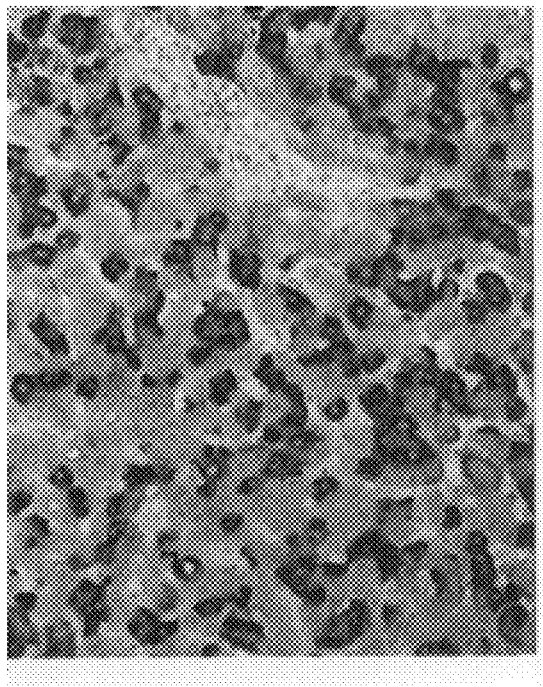
FIG. 1B
FIG.1C

FIG. 8

Row 1:
| Ala | Asp | Ile | Val | Met | Thr | Gln | Ser | Pro | Leu | Ser | Leu | Ser | Val | Thr | Pro | Gly | Glu | Pro |
|---|---|---|---|---|---|---|---|---|---|---|---|---|---|---|---|---|---|---|
| GCC | GAT | ATT | GTG | ATG | ACT | CAG | TCT | CCA | CTC | TCC | CTG | TCC | GTC | ACC | CCT | GGA | GAG | CCG |
|  |  |  | 9 |  |  | 18 |  |  | 27 |  |  | 36 |  |  | 45 |  |  | 54 |

Row 2:
| Ser | Trp | Ile | Cys | Arg | Ser | Gln | Gln | Ser | Leu | Leu | His | Arg | Ser | Gly | Asn | Asn | Tyr | Leu |
|---|---|---|---|---|---|---|---|---|---|---|---|---|---|---|---|---|---|---|
| TCC | TGG | ATC | TGC | AGG | TCT | CAG | CAG | AGC | CTC | CTG | CAT | AGG | TCT | GGA | AAC | AAC | TAT | TTG |
|  |  | 63 |  | 72 |  | 81 |  |  | 90 |  |  |  | 99 |  |  | 108 |  |  |

Row 3:
| Asp | Tyr | Leu | Gln | Pro | Gly | His | His | Ser | Pro | Leu | Leu | Gln | Ile | Tyr | Val | Gly | Ser | Asn |
|---|---|---|---|---|---|---|---|---|---|---|---|---|---|---|---|---|---|---|
| GAT | TAC | CTG | CAG | CCA | GGG | CAC | CAC | TCT | CCA | CTC | CTG | CAG | ATC | TAT | GTG | GGT | TCT | AAT |
|  | 123 |  | 132 |  |  | 141 |  |  | 150 |  |  |  | 159 |  |  | 168 |  |  |

Row 4:
| Arg | Ser | Ala | Gly | Val | Pro | Arg | Asp | Phe | Ser | Ser | Gly | Ser | Gly | Thr | Glu | Tyr | Thr | Leu |
|---|---|---|---|---|---|---|---|---|---|---|---|---|---|---|---|---|---|---|
| CGG | TCC | GCC | GGG | GTC | CCT | AGG | GAT | TTC | AGT | AGT | GGA | TCA | GGC | ACA | GAG | TAT | ACA | CTG |
|  | 183 |  | 192 |  |  | 201 |  |  | 210 |  |  |  | 219 |  |  | 228 |  |  |

Row 5:
| Lys | Ile | Ser | Arg | Val | Glu | Ala | Glu | Asp | Val | Gly | Val | Tyr | Tyr | Cys | Met | Gln | Ala | Leu |
|---|---|---|---|---|---|---|---|---|---|---|---|---|---|---|---|---|---|---|
| AAA | ATC | AGT | AGA | GTG | GAG | GCT | GAG | GAT | GTT | GGG | GTA | TAT | TAC | TGC | ATG | CAA | GCT | CTA |
|  | 243 |  | 252 |  | 261 |  | 270 |  |  | 279 |  |  |  | 288 |  |  |  |  |

Row 6:
| Thr | Pro | Arg | Thr | Phe | Gly | Gln | Gly | Thr | Lys | Leu | Glu | Ile | Lys |
|---|---|---|---|---|---|---|---|---|---|---|---|---|---|
| ACT | CCT | CGG | ACT | TTT | GGC | CAG | GGG | ACC | AAG | CTG | GAG | ATC | AAA |
|  |  | 303 |  |  | 312 |  |  | 321 |  |  | 330 |  |  |

FIG. 9

| Gln CAG | Val GTG | Leu CTG | Gly GGG | Ser TCA | Val GTG | Gly GGA | Gly GGC | Val GTG | Arg CGG | Pro CCT | Gly GGG | Arg AGG | Ser TCC | Leu CTG | Arg AGA |
|---|---|---|---|---|---|---|---|---|---|---|---|---|---|---|---|
| 9 | | 18 | | 27 | | 36 | | 45 | | 54 | | | | | |

Leu CTC / Ser TCC / Gln CAG / Val GTG / Leu CTG / Val GTG / Glu GAG / Ser TCA / Gly GGG / Gly GGA / Gly GGC / Val GTG / Val GTC / Arg CGG / Pro CCT / Gly GGG / Arg AGG / Ser TCC / Leu CTG / Arg AGA

| Cys TGT | Ala GCA | Ala GCC | Ser TCT | Gly GGA | Phe TTC | Phe TTC | Ala GCC | Asp GAC | Ser AGT | Ile ATA | Asn AAC | Trp TGG | Val GTC | Arg CGC | Gln CAG | Ala GCT |
|---|---|---|---|---|---|---|---|---|---|---|---|---|---|---|---|---|
| 66 | | 75 | | 84 | | 93 | | 102 | | 111 | | 120 | | | | |

Pro CCA / Gly GGC / Ala GCC / Ser TCT / Gly GGA / Phe TTC / Ala GCC / Ser TCA / Asp GAC / Tyr TAT / Ser AGT / Ile ATA / Asn AAC / Trp TGG / Val GTC / Arg CGC / Gln CAG / Ala GCT

| Lys AAG | Gly GGA | Leu CTG | Glu GAG | Trp TGG | Val GTG | Ala GCA | Ile ATT | Ile ATT | Ile ATT | Gly GGA | Arg AGA | Thr ACA | Tyr TAC | Tyr TAT | Arg AGA |
|---|---|---|---|---|---|---|---|---|---|---|---|---|---|---|---|
| 129 | | 138 | | 147 | | 156 | | 165 | | 174 | | 183 | | | |

Lys AAG / Gly GGA / Leu CTG / Glu GAG / Trp TGG / Val GTG / Ala GCA / Ala GCT / Ile ATT / Ser TCA / Ile ATT / Asp GAT / Tyr TAT / Gly GGA / Arg AGA / Thr ACA / Tyr TAC / Tyr TAT / Arg AGA

| Val GTG | Arg AGA | Phe TTC | Arg CGA | Thr ACC | Ile ATC | Ser TCC | Arg AGA | Asp GAT | Ser TCC | Leu CTG | Gln CAA |
|---|---|---|---|---|---|---|---|---|---|---|---|
| 192 | | 201 | | 210 | | 219 | | 228 | | 237 | 246 |

Asp GAC / Ser TCC / Lys AAG / Gly GGC / Val GTG / Arg AGA / Phe TTC / Thr ACC / Arg CGA / Ile ATC / Ala GCA / Ala GCT / Thr ACC / Asp GAC / Ser TCC / Arg AGA / Ala GCG / Asn AAC / Thr ACG / Leu CTG / Tyr TAT / Leu CTG / Gln CAA

| Ser AGC | Leu CTG | Thr ACT | Glu GAG | Asp GAC | Thr ACG | Cys TGC | Tyr TAC | Tyr TAT | Tyr TAT | Tyr TAC | Tyr TAT | Leu CTG | Phe TTT |
|---|---|---|---|---|---|---|---|---|---|---|---|---|---|
| 255 | | 264 | | 273 | | 282 | | 291 | | 300 | | 309 | |

Met ATG / Asn AAC / Ser AGC / Leu CTG / Thr ACT / Glu GAG / Asp GAC / Thr ACG / Ala GCT / Thr ACG / Asp GAC / Tyr TAT / Tyr TAC / Cys TGC / Tyr TAC / Ala GCG / Arg AGA / Gln CAG / Tyr TAT / Tyr TAT / Tyr TAC / Leu CTG / Phe TTT

| Gly GGT | Ser TCT | Ser TCG | Val GTT | Gly GGG | Tyr TAC | Arg CGT | Asn AAC | Gly GGC | Met ATG | Asp GAC | Ala GCG | Val GTC | Trp TGG | Gly GGC | Leu CTA | Gly GGG | Thr ACC | Thr ACG |
|---|---|---|---|---|---|---|---|---|---|---|---|---|---|---|---|---|---|---|
| 318 | | 327 | | 336 | | 345 | | 354 | | 363 | | 372 | | | | | | |

Trp TGG / Ser AGT / Gly GGT / Ser TCT / Ser TCG / Val GTT / Gly GGG / Arg CGT / Asn AAC / Tyr TAC / Asp GAC / Gly GGC / Met ATG / Asp GAC / Ala GCG / Val GTC / Trp TGG / Gly GGC / Leu CTA / Gly GGG / Thr ACC / Thr ACG

Val GTC / Thr ACC / Val GTC / Ser TCA

381

HUMAN MONOCLONAL ANTIBODY AGAINST HEPATITIS B VIRUS SURFACE ANTIGEN (HBVSAG)

FIELD OF THE INVENTION

The present invention concerns a hybridoma cell line producing human antibodies capable of binding to the hepatitis B virus surface antigen, antibodies produced by the cell lines, and various uses thereof.

BACKGROUND OF THE INVENTION

Hepatitis B virus (HBV) infection is a major worldwide health problem. Approximately 5% of the world population is infected by HBV and chronically infected patients carry a high risk of developing cirrhosis and hepatocellular carcinoma. (Progressive Hepatitis Research: Hepatitis B virus (HBV), Hepatitis C virus (HCV) and Hepatitis Delta virus (HDV) Ed. O. Crivelli, Sorina Biomedica, 1991).

The immune response to HBV-encoded antigens includes both a cellular immune response which is active in the elimination of HBV infected cells, as well as a humoral antibody response to viral envelope antigens which contributes to the clearance of circulating virus particles. The dominant cause of viral persistence during HBV infection is the development of a weak antiviral immune response.

Recombinant HBV vaccines provide a safe and effective means for active immunization against HBV, however, they do not always induce a sufficient and rapid antibody response.

Interferon-α has been used in the therapy of Hepatitis B infection showing an efficacy of only 30–40% in highly selected patients.

In addition, passive immunization with human polyclonal anti Hepatitis B antisera has been shown to be effective in delaying and even preventing recurrent HBV infection (Wright, T. L. and Lau, J. Y. N. The Lancet 342:1340–1344, (1993)). Such human polyclonal antisera are prepared from pooled plasma of immunized donors. These preparations are very expensive and available in relatively small amounts. Furthermore, pooled plasma may contain contaminated blood samples and thus treatment with such antisera increases the patient's risk to contract other viral infections such as hepatitis C or HIV.

An alternative approach for the treatment of HBV infections concerns the use of monoclonal antibodies (MoAb).

PCT patent application PCT/NL94/00102 discloses human monoclonal antibodies directed against Hepatitis B surface antigen which are secreted by the hybridoma cell lines Mab 4-7B and Mab 9H9. The monoclonal antibody secreted by the cell line Mab 4-7B recognizes a linear epitope of HBVsAg and is different from the Mab 9H9 monoclonal antibody which recognizes a conformational epitope. The antibodies are claimed for simultaneous use in the treatment of chronic Hepatitis B infections.

PCT patent application PCT/US92/09749 discloses human monoclonal antibodies against HBVsAg which are secreted by the hybridoma cell lines PE1-1, ZM1-1, ZM1-2, MD3-4 and LO3-3. The antibodies bind to different HBV epitopes and are used for reducing the level of circulating HBVsAg.

Japanese Patent Application JP 93066104 discloses a hybridoma of a human lymphocyte cell strain TAW-925 and a human lymphocyte transformed by Epstein-Barr virus. The hybridoma produces a human monoclonal antibody against HBVsAg.

U.S. patent application Ser. No. 4,883,752 discloses preparation of human-derived monoclonal antibody to HBVsAg, by administration of HBVsAg vaccine to humans, recovering their lymphocytes, stimulating the lymphocytes in vitro by a non specific stimulator, fusing said cells with a myeloma cell, and selecting for hybridomas with secrete anti HBVsAg antibodies.

Ichimori et al., Biochem. and Biophysic. Research Communications 129(1):26–33, 1985 discloses a hybridoma secreting human anti HBVsAg monoclonal antibodies which recognize the a-determinant of HBVsAg. Later, Ichimori, et al., supra 142(3):805–812, 1987 disclosed another hybridoma which stably secretes human monoclonal antibody against HBsAg.

SUMMARY OF THE INVENTION

In accordance with the present invention, a hybridoma cell line is provided which secretes human antibodies capable of binding to the Hepatitis B surface antigen (HBVsAg).

In accordance with the invention, peripheral blood lymphocytes (PBL) were obtained from human individuals having a high titer of anti HBVsAg antibodies. Such individuals may either have been previously infected with HBV, actively immunized with HBV antigens or spontaneously showing a high level of such antibodies. A most preferred human donor is an individual which tested negative for the presence of HBV but shows a high titer of antibodies against HBVsAg. PBLs from the human donor may be obtained either by whole blood donation or by leukophoresis.

The human PBLs are then activated in vitro by their incubation with pokeweed mitogen (PWM). After activation the PBLs are fused in vitro preferably with a human-mouse fusion partner such as a heteromyeloma by techniques well known in the art (e.g. Kohler & Milstein, Nature, 256:495–497, 1975). The generated hybridoma cell lines are either cultured in vitro in a suitable medium wherein the desired monoclonal antibody is recovered from the supernatant or, alternatively the hybridoma cell lines may be injected intraperitoneally into mice and the antibodies harvested from the malignant ascitis or serum of these mice. The supernatant of the hybridoma cell lines are first screened for production of human IgG antibodies by any of the methods known in the art such as enzyme linked immunosorbent assay (ELISA) or radioimmuno assay (RIA). Hybridomas testing positive for human IgG are then further screened for production of anti HBVsAg antibodies by their capability to bind to HBVsAg.

In accordance with the preferred embodiment of the present invention, a hybridoma cell line designated herein as "17.1.41" which was deposited on May 22, 1996, at the European Collection of Cell Cultures (ECACC, CAMR, Salisbury, Wiltshire, SP40JG, U.K.) under the Accession No. 96052169 is provided. Anti HBVsAg human monoclonal antibodies secreted by the above hybridoma cell line designated herein as "Ab17.1.41" as well as fragments thereof retaining the antigen binding characteristics of the antibodies and antibodies capable of binding to the antigenic epitope bound by Ab17.1.41 are also provided. Such fragments may be, for example, Fab or $F(ab)_2$ fragments obtained by digestion of the whole antibody with various enzymes as known and described extensively in the art. The antigenic characteristics of an antibody are determined by testing the binding of an antibody to a certain antigenic determinant using standard assays such as RIA, ELISA or FACS analysis.

The antibodies of the invention have a relatively high affinity to HBVsAg being in the range of about $10^{-9}$M to about $10^{-10}$M as determined by a competitive ELISA assay.

The antigen bound by the antibodies defined above also constitutes an aspect of the invention.

Further aspects of the present invention are various diagnostic prophylactic and therapeutic uses of the Ab 17.1.41 monoclonal antibodies and the Ag bound by these antibodies. In accordance with this aspect of the invention, pharmaceutical compositions comprising the Ab17.1.41 antibodies may be used for the treatment of chronic Hepatitis B patients by administering to such a patient a therapeutically effective amount of the antibodies or fragments thereof capable of binding to the HBVsAg being an amount effective in alleviating the symptoms of the HBV infection or reducing the number of circulating viral particles in an individual.

In addition to the antibodies of the invention the pharmaceutical compositions may optionally also comprise a carrier selected from any of the carriers known in the art. One example of such a carrier is a liposome. The pharmaceutical compositions of the invention may also comprise various diluents and adjuvants known per se.

The compositions of the invention may be administered by a variety of administration modes including parenterally, orally etc. Compositions comprising the antibodies of the invention, as described above, may be administered in combination with other anti viral agents. Such agents may include, as a non limiting example: Interferons, anti HB monoclonal antibodies, anti HB polyclonal antibodies, nucleoside analogs, and inhibitors of DNA polymerase. In the case of such a combination therapy the antibodies may be given simultaneously with the anti viral agent or sequentially either before or after treatment with the anti viral agent.

Such pharmaceutical compositions may also be used, for example, for immunization of new born babies against HBV infections or for immunization cf liver transplantation patients to eliminate possible recurrent HBV infections in such patients.

By a further embodiment, the antibodies of the invention may also be used in a method for the diagnosis of HBV infections in an individual by obtaining a body fluid sample from the tested individual which may be a blood sample, a lymph sample or any other body fluid sample and contacting the body fluid sample with a human anti HBVsAg antibody of the invention under conditions enabling the formation of antibody-antigen complexes. The level of such complexes is then determined by methods known in the art, a level significantly higher than that formed in a control sample indicating an HV infection in the tested individual. In the same manner, the specific antigen bound by the antibodies of the invention may also be used for diagnosis of HB infection in an individual by contacting a body fluid sample from the tested individual with the antigen as described above and determining the formation of antigen Ab in the sample.

BRIEF DESCRIPTION OF THE DRAWINGS

FIG. 1 is a photograph showing Hepatitis B infected liver sections stained with the anti HBVs antibodies of the invention. All sections were stained with a "secondary" antibody, i.e. goat anti human or anti mouse Ig conjugated to biotin.

A—negative control. No first antibody.

B—positive control. First antibody—mouse anti HB antibody and a secondary anti-mouse Ig.

C—staining with anti HBVsAg Ab 17.1.41.

Reference will now be made to the following Examples which are provided by way of illustration and are not intended to be limiting to the present invention.

Figure 2:
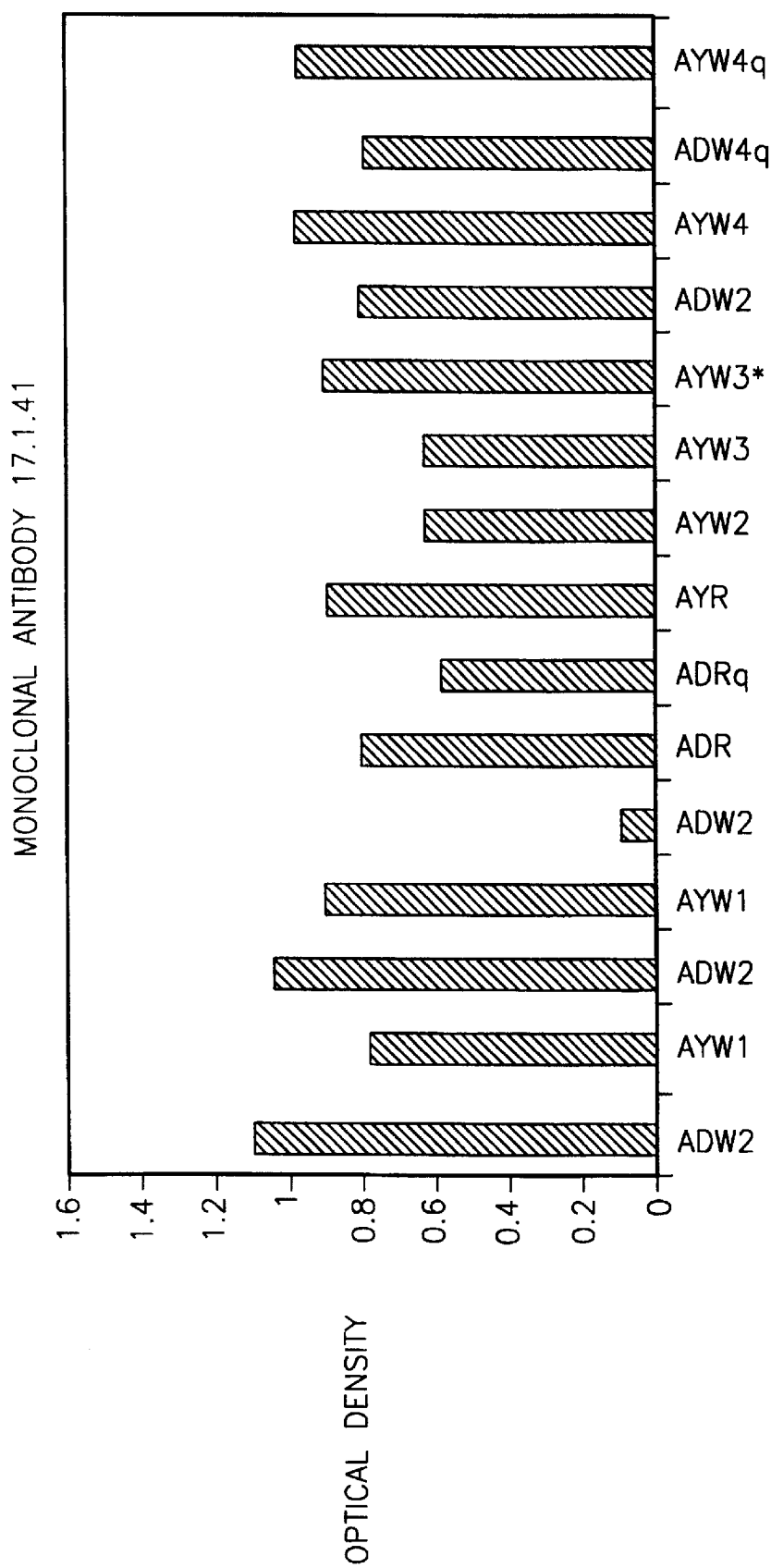

FIG. 2 is a schematic representation of the binding of Ab17.1.41 to a set of well characterized HBsAg types. The y axis represents optical density units. The x axis represents different HBsAg types.

Figure 3:
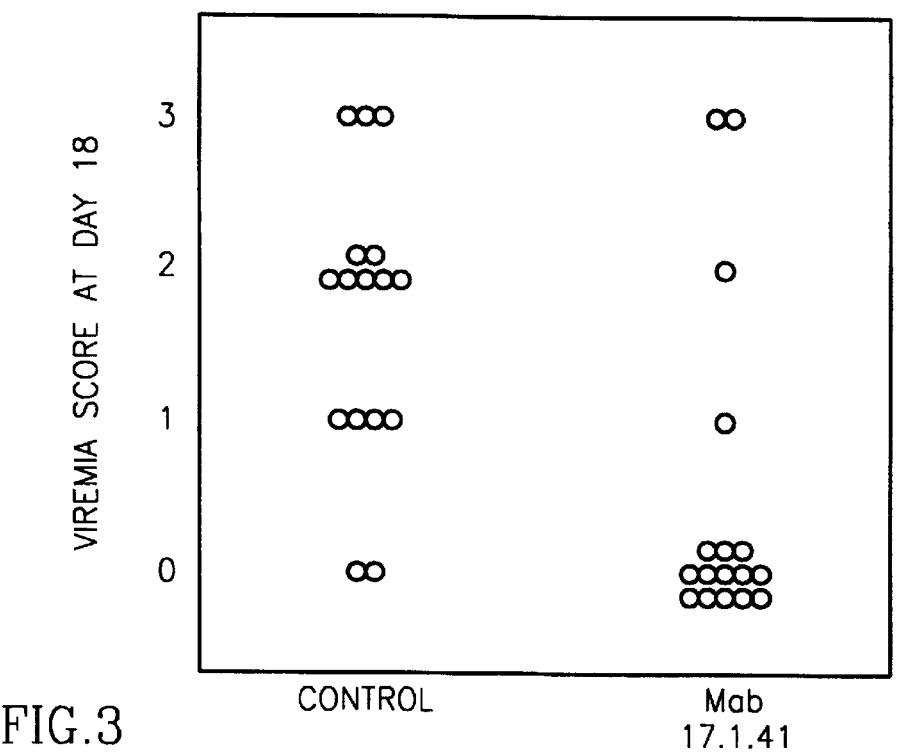

FIG. 3 is a graphic representation of hepatitis B viremia score, as defined in example 3. Each dot in the graph represents one animal.

Figure 4:
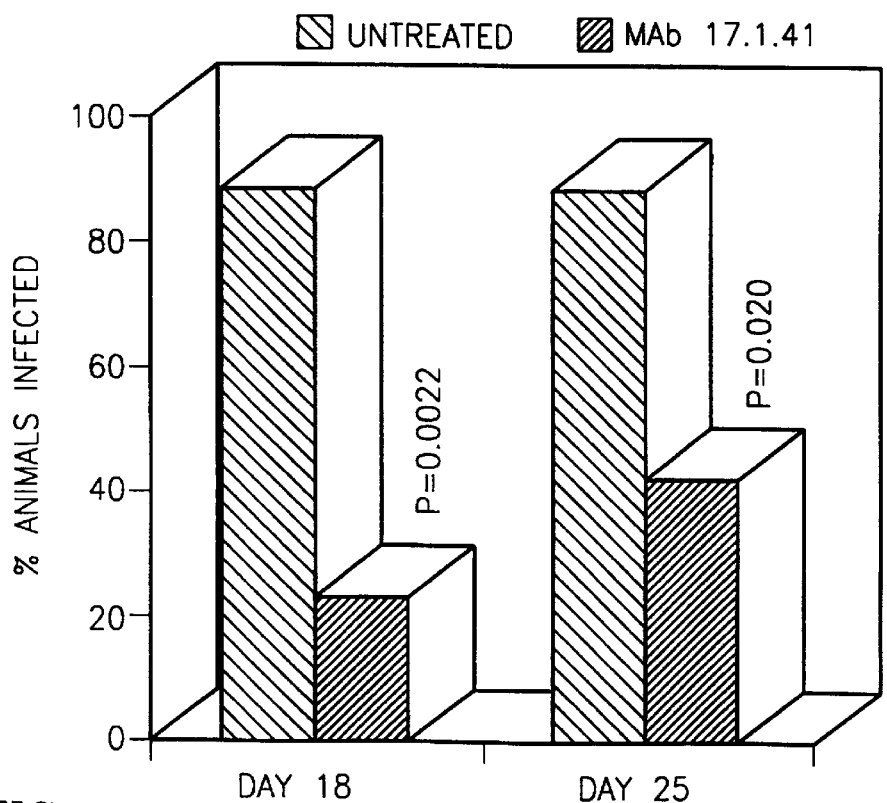

FIG. 4 is a graphic representation of the percentage of HBV infected animals at days 18 and 25 in the untreated group and Ab17.1.41 treated group (in the treatment model).

Figure 5:
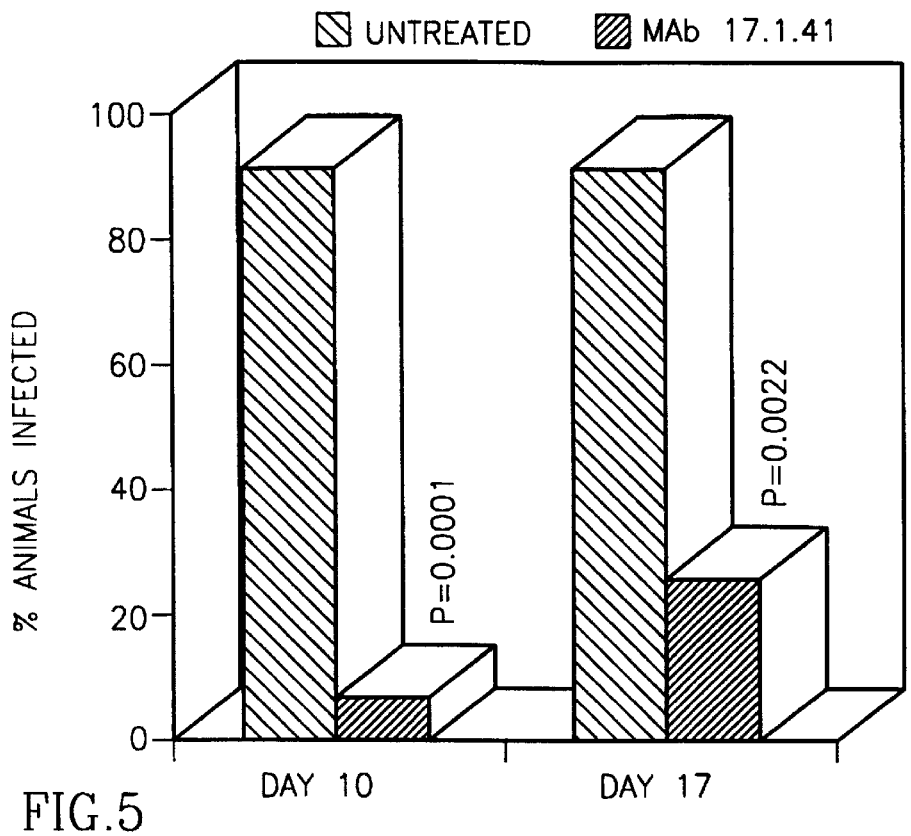

FIG. 5 is a graphic representation of the percentage of HBV infected animals at days 10 and 17 in the untreated group and Ab17.1.41 treated group (in the combined prophylaxis/inhibition model).

Figure 6:
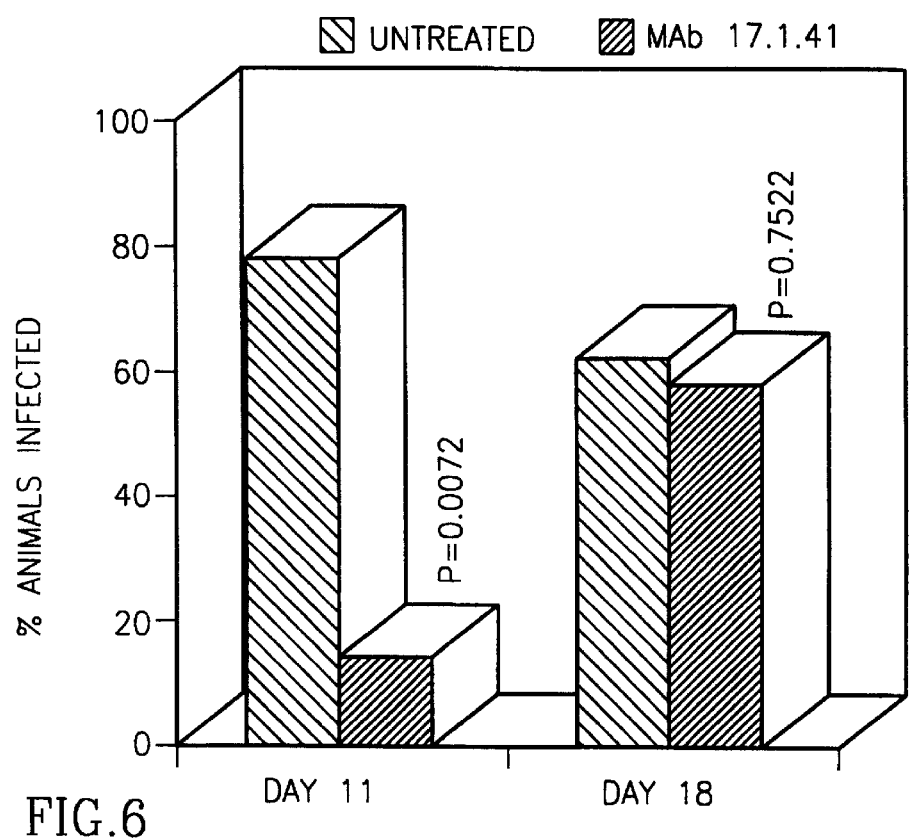

FIG. 6 is a graphic representation of the percentage of HBV infected animals at days 11 and 18 in the untreated group and Ab 17.1.41 treated group (in the combined inhibition/treatment model).

Figure 7:
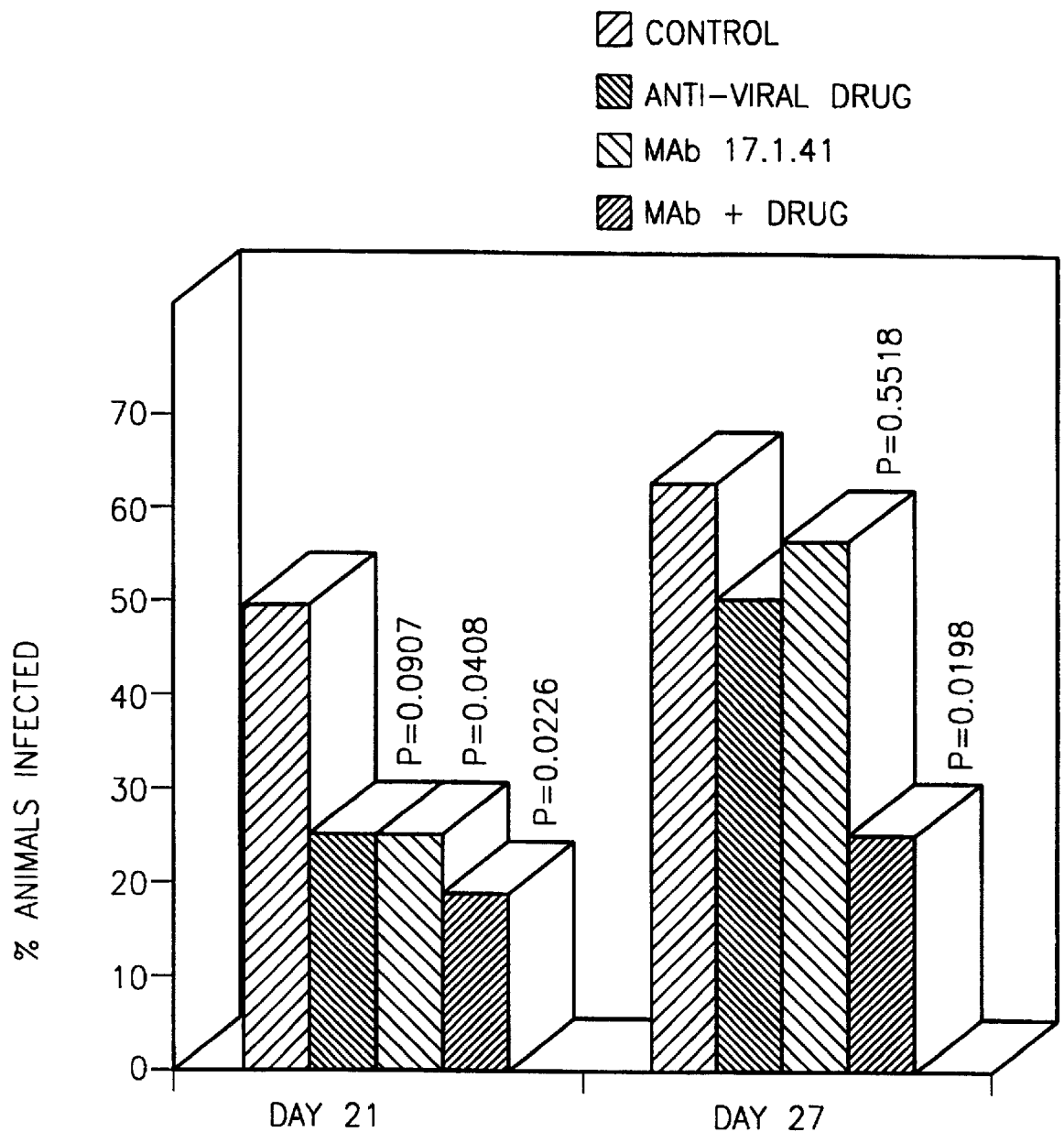

FIG. 7 is a graphic representation of the percentage of HBV infected animals at days 21 and 27 in the untreated group (control), the group treated with an anti viral drug, the group treated with Ab17.1.41 and the group treated with both the anti viral drug and Ab17.1.41 (Mab+Drug).

FIG. 8 Nucleic acid sequence (SEQ ID NO:1) and corresponding amino acid sequence (SEQ ID NO:2) of the light chain of the variable domain of Ab17.1.4 1.

FIG. 9 Nucleic acid sequence (SEQ ID NO:3) and corresponding amino acid sequence (SEQ ID NO:4) of the heavy chain of the variable domain of Ab 17.1.41.

EXAMPLES

Materials and Methods

In vitro Activation:

Peripheral blood lymphocytes (PBL) were obtained after informed consent by leukophoresis from donors positive for HBs antibodies and negative for HBV. PBLs were washed twice, counted and resuspended in PBS to the desired cell concentration. PBL were separated from granulocytes and erythrocytes on a Ficoll-hypaque gradient (UNI-SEP maxi; Eldan Tech., Jerusalem, Israel) and subsequently stimulated for 3–4 days with pokeweed mitogen (PWM; Gibco BRL, Life Technologies Inc., Grand Island, N.Y.) diluted 1:100 and with Antigen at 200 ng/ml in RPMI-1640 medium with 10% (v/v) fetal calf serum (FCS) supplemented with 10 U/ml penicillin, 10 µg/ml streptomycin, 2 mM L-glutamine, 1 mM sodium pyruvate, 1% (v/v) non-essential amino acids (Biological Industries, Beit Haemek, Israel) and $10^{-4}$ M 2-mercaptoethanol (Sigma, St. Louis) (Complete Medium).

Cell Fusion:

Cells were mixed with the human-mouse heteromyeloma HMMA2.1 1TG/0 (Posner et al.) at 3:1 ratio. Fusion was performed with 50% (w/v) PEG 1500 (Boehringer Manheim GmbH) in a standard procedure. Fused cells were seeded at a concentration of 30000 cells/well in 96-well U-bottom microtiter plates (Nunc, Denmark) in complete medium containing HAT-supplement (1×) (Biological Industries, Beit Haemek, Israel). Cells were fed with fresh HAT-medium a week latter. Two weeks after fusion supernatants were harvested for ELISA and medium was replaced with fresh HT-medium.

Hybridoma cultures secreting specific anti-HBs Ig were cloned at 0.5 cell/well in 96-well U-bottom microtiter plates.

Determination of Human Immunoglobulin:

Sera were tested for antigen specific and total human ig. Total human Ig was quantified by sandwich ELISA using goat F(ab)$_2$-purified anti-human IgG+IgM+IgA (Zymed Laboratories, San Francisco, Calif.) as the capture agent and peroxidase-conjugated purified goat anti-human (Zymed Laboratories) as the detection reagent. Human serum of known immunoglobulin concentration was used as the standard (Sigma, Rehovot, Israel). Microplates (Nunc, Roskilde, Denmark) pre-coated with the capture reagent (2.5 ug/ml, 50 ul/well) and blocked with 1% BSA were incubated overnight at 4C with dilutions of plasma from 1:20000 to 1:640000, or the standard from 0.2 to 0.06 ug/ml, then washed 5 times with PBS-Tween solution. The detection reagent was added and the plates were incubated for 1 h at 37C, then washed again 3 times. Fresh substrate solution (TMB, Sigma) was added and, after peroxidase-catalyzed color development, the reaction was stopped by addition of 10% sulfuric acid. Absorbance at 450 nm was quantified on an ELISA reader (Dynatech, Port Guernsey, Channel Islands, UK).

Concentration of antigen-specific human antibodies in mice sera was determined by HBsAb EIA kit (ZER, Jerusalem, Israel).

Human antibodies in hybridoma supernatants were determined by overnight incubation of supernatants on goat anti-human IgG+A+M (Zymed) coated plates, with goat anti-human IgG-peroxidase conjugated as the secondary reagent.

Antigen-specific antibodies in hybridoma supernatants were determined as above using Hbs antigen coated plates.
Determination of Human IgG Subclasses:
Human IgG subclasses were determined by sandwich ELISA using goat F(ab)$_2$-purified anti-human IgG+IgM+ IgA (Zymed Laboratories, San Francisco, Calif.) coated plates and Hbs antigen coated plates. Mouse anti-human IgG subclasses (Sigma) were used as second antibody and peroxidase-conjugated purified goat anti-human (Zymed Laboratories) as the detection reagent.
Statistic Analysis:

Statistical analysis was performed using the Stat View II program (Abacus Concepts, Inc., Berkeley, Calif.) on a Mackintosh Quadra 605 or Microsoft Excel 5.0 (Microsoft) on a 486 DX2 PC compatible. Student t-test, Anova correlation and regression analysis were utilized to calculate probability (p) and correlation coefficient (r) values. Results are presented as mean ± standard error.
Affinity Constant Measurements:

Determination of affinity constants (K$_D$) of the different anti-HBs antibodies to ad antigen (Chemicon Cat. No. AG 850) in solution were performed according to Friguet et al. (*Journal of Immunological Methods*, 77:305–319, 1985). The antigen at various concentrations (3.5×10$^{-10}$M to 1.4× 10$^{-9}$M) was first incubated in solution with a constant amount of antibody (3.4×10$^{-11}$M), in 0.1 M sodium phosphate buffer containing 2 mM EDTA and 10 mg/ml BSA, pH 7.8 (medium buffer). After o.n. incubation at 20 C the concentration of free antibody was determined by an indirect ELISA. A volume of 300 ul of each mixture were transferred and incubated for 2 h at 20 C into the wells of a microtitration plate (Nunc) previously coated with Ad (50 μl/well at 1 μg/ml in 0.1 M NaHCO$_3$ buffer, pH 9.6 for 2 h at 37° C.). After washing with PBS containing 0.04% Tween 20, the bound antibodies were detected by adding HRP-F(ab')$_2$ Goat anti human IgG (Zymed) diluted 1:3000 with medium buffer, 50 μl/well 2 h at 20° C. The plate was developed with TMB chromogen (Sigma T-3405 tablets) 50 μl/well, the reaction stopped with 10% H$_2$SO$_4$ 50 μl/well and the plate read in an ELISA reader at 450 nm. The conditions were chosen so that the resulting f values (see Friguet et al.) were around 0.1. The antibody concentration used was deduced from an ELISA calibration done on the same plate. The affinity constant KD was calculated from the relevant Scatchard plot.
Inhibition Assays:

The inhibition assay was performed in microtiter plates coated with HBs particles (2 μg/ml in PBS). The plate was blocked with 3% BSA in PBS. Hybridoma supernatants containing anti HBs antibodies were serially diluted. 50 μl of each dilution were added to the coated microtiter wells. Subsequently, 50 μl of HBs particles (ad/ay, 0.5 μl/ml in PBS) or PBS alone were added to each well. The plates were incubated overnight at room temperature in a humid chamber and washed 5 times with PBS-Tween. Next, 50 μl of goat anti human IgG conjugated to HRP (diluted 1:5000 in PBS) were added to each well. After a 4 hour incubation at room temperature in a humid chamber the plates were washed 5 times with PBS-Tween, and TMB was added to each well. Results were read using an ELISA reader, in a wavelength of 450 nm.
Immunohistostaining:

HBV positive liver fragment was fixed in 4% neutral buffered formaldehyde for 24 h and then embedded in paraffin using routine procedures. Section of 4 μm thickness were cut from paraffin blocks and mounted on polylysine-coated slides. After deparaffinization and peroxidase quenching staining was performed using our monoclonal Human anti-HBs Protein A-purified antibodies followed by biotinylated Goat anti-Human IgG (H+L) (Zymed, San Francisco, Calif.) using Histostain-SPTM kit (Zymed) according to the manufacture's recommendation. Control slides without using the 1 st Human anti-HBs antibody were stained in parallel.
Sequence analysis:

Total RNA was isolated from 10×10$^6$ hybridoma cells with RNAsol B reagent (TEL-TEX, Inc. Friendswood, Tex.). cDNA was prepared from 10 μg of total RNA with reverse transcriptase and oligo dT (Promega, Madison, Wis.) according to standard procedures. PCR was performed on 1/50 of the RT reaction mixture with V$_H$, V$_\lambda$ or V$_\kappa$5' leader primers and 3' primers corresponding to human constant region. The PCR fragments were cloned into pGEM-T vector (Promega). The inserts were sequenced using an ABI 377 sequencing machine. Sequences were analyzed by comparison to Genbank and by alignment to Kabat sequences (Kabat et al. 1991, Sequences of proteins of immunological interest (5$^{th}$ Ed.) U.S. Dept. of Health and Human Services, National Institutes of Health, Bethesda, Md.).

Example 1

Human peripheral blood lymphocytes (PBL) from donors positive for anti HBVs antibodies were obtained and activated in vitro with PWM as described above. The cells were then fused with a human mouse heteromyeloto form hybridoma cell lines. One stable hybridoma clone secreting specific human anti HBVsAg designated 17.1.41 was characterized. The antibodies secreted by the above clone were purified on a protein A column as well as on an anti human Ig-agarose column and were found to be of the IgG1 Vκ type. The affinity constant of the antibodies to HBVsAg was 1.34×10$^{-9}$. Specificity was tested by competitive inhibition assay using HBV surface antigen of the ad-ay (1:1).

Example 2

The 17.1.41 antibodies were used for staining human liver fragments as described above. As seen in FIG. 1, the 17.1.41 antibodies were able to detect HBV particles present in the infected liver fragments.

The gene encoding the variable region of Ab 17.1.41 was isolated, fully sequenced, and its subgroups and CDRs were determined.

The antibody has a fully human Ig gene sequence as determined by alignment to Genebank sequences and Kabat protein sequences. FIG. 8 shows the nucleotide sequence of the cDNA encoding the light chain of the variable region of Ab 17.1.41 and its corresponding amino acid sequence (Sequence identification nos. I and 3). FIG. 9 shows the nucleotide sequence of the cDNA encoding the heavy chain of the variable region of Ab17.1.41 and its corresponding amino acid sequence (Sequence identification nos. 2 and 4).

The sequencing data reveled that the variable region of Ab 17.1.41 consists of the subgroups $V_{H3}$, $J_H6$, $V_{\kappa2}$ and $J_{\kappa2}$.

HBV genomes are classified into six groups A to F, based on the degree of similarity in their nucleotide sequences. The genetic variability of HBV is further reflected in the occurrence of different serotypes of HBsAg. The common determinant 'a' and two pairs of mutually exclusive determinants 'd/y' and 'w/r' enable the distinction of four major subtypes of HBsAg: adw, adr, ayw and ayr. Additional determinants designated subdeterminants of w(w1 to w4) have allowed the definition of four serotypes of ayw (ayw1–4) and two serotypes of adw, i.e. adw2 and adw4. Additional subtype variation is added by the q determinant, which is present on almost all subtypes. Its absence is marked by a 'q−' sign. The kind of HBV serotypes recognized by Ab 17.1.41 was examined using a set of 15 different HBsAg types (Norder et al., 1992, Journal of General Virology, 73, 3141; Magnius and Norder, 1995, Intervirology, 38, 24–34). As can be seen in FIG. 2, Ab 17.1.41 has a broad reactivity towards all tested subtypes and genotypes, except for C adw2.

Example 3

The biological activity of Ab 17.1.41 was characterized using the following HBV animal model: a mouse was treated so as to allow the stable engraftment of human liver fragments. The treatment included intensive irradiation followed by transplantation of scid (severe combined immunodeficient) mice bone marrow. Viral infection of human liver fragments was performed ex-vivo using HBV positive human serum (EP 699 235).

The animal model was used in three different modes representing various potential uses of the antibodies: treatment mode, combined prophylaxis/inhibition mode and combined inhibition/treatment.

1. Treatment mode—This model demonstrates the ability to use the antibody to treat chronic HBV infection. Mice were transplanted with HBV infected human liver fragments. The mice were treated with Ab 17.1.41 at days 16, and 17 post liver transplantation. HBV DNA was tested on days 18 and 25. The number of HBV DNA copies (the viral load) in mouse sera was determined using PCR. We use the term "viremia score" as a mathematical representation of the viral load. The viremia score was determined as follows:

| Viremia score | viral load = HBV DNA copies/ml serum |
|---|---|
| 0 | viral load $< 5 \times 10^3$ |
| 1 | $5 \times 10^3 <$ viral load $< 5 \times 10^4$ |
| 2 | $5 \times 10^4 <$ viral Ioad $< 5 \times 10^5$ |
| 3 | viral load $> 5 \times 10^5$ |

As can be seen in FIG. 3, there is a significant reduction in the viremia score in the group treated with the antibody. In addition, as can be seen in FIG. 4, the percentage of infected animals in the treated group are significantly lower (very low p values) as compared to the untreated group.

2. Combined prophylaxis/inhibition mode—This model represents liver transplantation. In this model mice were treated with Ab 17.1.41 (10 I.U./mouse) three days before liver transplantation followed by transplantation of human liver fragments which were ex vivo infected with HBV in the presence of Ab 17.1.41 (100 I.U.). HBV DNA was tested in mice sera 10 and 17 days after transplantation. As can be seen in FIG. 5, there was a significant reduction in the percentage of infected animals in the treated group compared to the control group.

3. Combined inhibition/treatment mode—a) HBV positive human serum was preincubated with Ab 17.1.41 followed by standard ex vivo liver infection. b) Mice were treated with Ab 17.1.41 at days 0 and 7 post transplantation. HBV DNA in mice sera was tested on days 11 and 18. As can be seen in FIG. 6, the percentage of infected animals in the Ab 17.1.41 treated group was significantly reduced but rebounded about two weeks after the treatment was stopped.

Example 4

In the following experiment we tested the possibility to use 17.1.41 in combination with another anti viral agent in the HBV model described above. Mice were treated with the anti viral drug (a nucleoside analogue, 0.5 mg/mouse/day) at days 17–20 post transplantation. A group of mice was further treated with Ab 17.1.41 at days 19 and 20. The presence of HBV DNA in mice sera was tested on days 21 and 27. As can be seen in FIG. 7, immediately after treatment either with the anti viral drug or with our monoclonal antibody there was a marked reduction in the number of animals infected. However, viral load rebounded in each group that was treated with one individual drug. Only the group that was treated with the combination of the anti viral drug and Ab 17.1.41 did not show an increase in the number of animals infected.

What is claimed is:

1. A human monoclonal antibody Ab17.1.41, which is secreted by the hybridoma cell line deposited in the European Collection of Cell Cultures (ECACC) under Accession No. 96052169.

2. The hybridoma cell line deposited at the ECACC on May 22, 1996 under Accession No. 96052169.

3. A pharmaceutical composition for the treatment of Hepatitis B Virus (HBV) infections comprising as an active ingredient an antibody in accordance with claim 1 together with a pharmaceutically acceptable carrier.

4. A method for the treatment of Hepatitis B Virus (HBV) infections comprising administering to an individual in need a therapeutically effective amount of antibodies according to claim 1.

5. A method for reducing the occurrence of Hepatitis B virus (HBV) infections in a population of individuals, comprising administering a human monoclonal antibody Ab 17.1.41 or a fragment thereof which retains the antigen binding characteristics of Ab 17.1.41 in accordance with claim 1 to a population of individuals to reduce the occurrence of HBV infections in the population.

6. A pharmaceutical composition for the treatment of Hepatitis B Virus infections comprising as an active ingredient an antibody in accordance with claim 1 adopted for use in combination with at least one other active ingredient being an anti viral agent.

7. A pharmaceutical composition according to claim 6 wherein the anti viral agent is selected from the group consisting of: interferons, anti-Hepatitis B (HB) monoclonal antibodies, anti HB polyclonal antibodies, nucleoside analogues and inhibitors of DNA polymerase.

8. A pharmaceutical composition according to claim 6 wherein the anti viral agent is a nucleoside analogue.

9. A method for the treatment of HBV infections comprising administering to an individual in need thereof a therapeutically effective amount of a pharmaceutical composition according to claim 6.

10. A method for the treatment of HBV infections comprising administering to an individual in need thereof a therapeutically effective amount of a pharmaceutical composition according to claim 7.

11. A method for the treatment of HBV infections comprising administering to an individual in need thereof a therapeutically effective amount of a pharmaceutical composition according to claim 8.

* * * * *

UNITED STATES PATENT AND TRADEMARK OFFICE
CERTIFICATE OF CORRECTION

| | |
|---|---|
| PATENT NO. | : 6,146,629 |
| APPLICATION NO. | : 09/000088 |
| DATED | : November 14, 2000 |
| INVENTOR(S) | : Shlomo Dagan |

It is certified that error appears in the above-identified patent and that said Letters Patent is hereby corrected as shown below:

Claim 1, line 4 (column 11, line 60), after "96052169" insert --, or a fragment thereof which retains the antigen binding characteristics of Ab 17.1.41--

Signed and Sealed this

Twenty-ninth Day of August, 2006

JON W. DUDAS
*Director of the United States Patent and Trademark Office*

SEQUENCE LISTING

<160> NUMBER OF SEQ ID NOS: 4

<210> SEQ ID NO 1
<211> LENGTH: 336
<212> TYPE: DNA
<213> ORGANISM: HUMAN
<220> FEATURE:

```
<221> NAME/KEY: CDS
<222> LOCATION: (1)..(336)

<400> SEQUENCE: 1 gat att gtg atg act cag tct cca ctc tcc ctg tcc gtc acc cct gga      48
Asp Ile Val Met Thr Gln Ser Pro Leu Ser Leu Ser Val Thr Pro Gly
 1               5                  10                  15 gag ccg gcc tcc atc tcc tgc agg tct agt cag agc ctc ctg cat agg      96
Glu Pro Ala Ser Ile Ser Cys Arg Ser Ser Gln Ser Leu Leu His Arg
             20                  25                  30 tct gga aac aac tat ttg gat tgg tac ctg cag aag cca ggg cac tct     144
Ser Gly Asn Asn Tyr Leu Asp Trp Tyr Leu Gln Lys Pro Gly His Ser
         35                  40                  45 cca cag ctc ctg atc tat gtg ggt tct aat cgg gcc tcc ggg gtc cct     192
Pro Gln Leu Leu Ile Tyr Val Gly Ser Asn Arg Ala Ser Gly Val Pro
     50                  55                  60 gac agg ttc agt ggc agt gga tca ggc aca gag tat aca ctg aaa atc     240
Asp Arg Phe Ser Gly Ser Gly Ser Gly Thr Glu Tyr Thr Leu Lys Ile
 65                  70                  75                  80 agt aga gtg gag gct gag gat gtt ggg gta tat tac tgc atg caa gct     288
Ser Arg Val Glu Ala Glu Asp Val Gly Val Tyr Tyr Cys Met Gln Ala
                 85                  90                  95 cta caa act cct cgg act ttt ggc cag ggg acc aag ctg gag atc aaa     336
Leu Gln Thr Pro Arg Thr Phe Gly Gln Gly Thr Lys Leu Glu Ile Lys
            100                 105                 110

<210> SEQ ID NO 2
<211> LENGTH: 112
<212> TYPE: PRT
<213> ORGANISM: HUMAN

<400> SEQUENCE: 2

Asp Ile Val Met Thr Gln Ser Pro Leu Ser Leu Ser Val Thr Pro Gly
 1               5                  10                  15

Glu Pro Ala Ser Ile Ser Cys Arg Ser Ser Gln Ser Leu Leu His Arg
             20                  25                  30

Ser Gly Asn Asn Tyr Leu Asp Trp Tyr Leu Gln Lys Pro Gly His Ser
         35                  40                  45

Pro Gln Leu Leu Ile Tyr Val Gly Ser Asn Arg Ala Ser Gly Val Pro
     50                  55                  60

Asp Arg Phe Ser Gly Ser Gly Ser Gly Thr Glu Tyr Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Arg Thr Phe Gly Gln Gly Thr Lys Leu Glu Ile Lys
            100                 105                 110

<210> SEQ ID NO 3
<211> LENGTH: 387
<212> TYPE: DNA
<213> ORGANISM: HUMAN
<220> FEATURE:
<221> NAME/KEY: CDS
<222> LOCATION: (1)..(387)

<400> SEQUENCE: 3 cag gtg cag ctg gtg gag tca ggg gga ggc gtg gtc cgg cct ggg agg      48
Gln Val Gln Leu Val Glu Ser Gly Gly Gly Val Val Arg Pro Gly Arg
 1               5                  10                  15 tcc ctg aga ctc tcc tgt gca gcc tct gga ttc gcc ttc agt gac tat      96
Ser Leu Arg Leu Ser Cys Ala Ala Ser Gly Phe Ala Phe Ser Asp Tyr
```

-continued

```
                    20                  25                  30
agt ata aac tgg gtc cgc cag gct cca ggc aag gga ctg gag tgg gtg     144
Ser Ile Asn Trp Val Arg Gln Ala Pro Gly Lys Gly Leu Glu Trp Val
            35                  40                  45 gca att att tca tat gat gga aga att aca tac tat aga gac tcc gtg     192
Ala Ile Ile Ser Tyr Asp Gly Arg Ile Thr Tyr Tyr Arg Asp Ser Val
        50                  55                  60 aag ggc cga ttc acc atc tcc aga gac gac tcc aag aac acg ctg tat     240
Lys Gly Arg Phe Thr Ile Ser Arg Asp Asp Ser Lys Asn Thr Leu Tyr
65                  70                  75                  80 ctg caa atg aac agc ctg aga act gag gac acg gct gtg tat tac tgc     288
Leu Gln Met Asn Ser Leu Arg Thr Glu Asp Thr Ala Val Tyr Tyr Cys
                85                  90                  95 gcg aga cag tat tac gat ttt tgg agt ggt tct tcg gtt ggg cgt aac     336
Ala Arg Gln Tyr Tyr Asp Phe Trp Ser Gly Ser Ser Val Gly Arg Asn
            100                 105                 110 tac gac ggc atg gac gtc tgg ggc cta ggg acc acg gtc acc gtc tcc     384
Tyr Asp Gly Met Asp Val Trp Gly Leu Gly Thr Thr Val Thr Val Ser
        115                 120                 125 tca                                                                  387
Ser
```

<210> SEQ ID NO 4
<211> LENGTH: 129
<212> TYPE: PRT
<213> ORGANISM: HUMAN

<400> SEQUENCE: 4

```
Gln Val Gln Leu Val Glu Ser Gly Gly Val Val Arg Pro Gly Arg
1               5                   10                  15

Ser Leu Arg Leu Ser Cys Ala Ala Ser Gly Phe Ala Phe Ser Asp Tyr
            20                  25                  30

Ser Ile Asn Trp Val Arg Gln Ala Pro Gly Lys Gly Leu Glu Trp Val
            35                  40                  45

Ala Ile Ile Ser Tyr Asp Gly Arg Ile Thr Tyr Tyr Arg Asp Ser Val
        50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Gln Tyr Tyr Asp Phe Trp Ser Gly Ser Ser Val Gly Arg Asn
            100                 105                 110

Tyr Asp Gly Met Asp Val Trp Gly Leu Gly Thr Thr Val Thr Val Ser
        115                 120                 125

Ser
```